United States Patent
Firger et al.

(10) Patent No.: US 10,912,758 B2
(45) Date of Patent: Feb. 9, 2021

(54) COMPOSITIONS WITH KETOGENIC AGENTS, CANNABINOIDS, PLANT-DERIVED SUBSTANCES AND MICRONUTRIENTS

(71) Applicants: Robert Firger, Bloomfield, CT (US); Gerald M. Haase, Denver, CO (US)

(72) Inventors: Robert Firger, Bloomfield, CT (US); Gerald M. Haase, Denver, CO (US)

( * ) Notice: Subject to any disclaimer, the term of this patent is extended or adjusted under 35 U.S.C. 154(b) by 0 days.

(21) Appl. No.: 16/350,664

(22) Filed: Dec. 19, 2018

(65) Prior Publication Data
US 2020/0197356 A1 Jun. 25, 2020

(51) Int. Cl.
| | |
|---|---|
| *A61K 31/352* | (2006.01) |
| *A61K 31/07* | (2006.01) |
| *A61P 3/02* | (2006.01) |
| *A61K 45/06* | (2006.01) |
| *A61K 36/73* | (2006.01) |
| *A61K 36/82* | (2006.01) |
| *A61K 36/63* | (2006.01) |
| *A61K 36/87* | (2006.01) |
| *A61K 36/534* | (2006.01) |

(52) U.S. Cl.
CPC ............ *A61K 31/352* (2013.01); *A61K 31/07* (2013.01); *A61K 45/06* (2013.01); *A61P 3/02* (2018.01); *A61K 36/534* (2013.01); *A61K 36/63* (2013.01); *A61K 36/73* (2013.01); *A61K 36/82* (2013.01); *A61K 36/87* (2013.01)

(58) Field of Classification Search
CPC ...... A61K 31/352; A61K 45/06; A61K 31/07; A61K 36/82; A61K 36/73; A61K 36/534; A61K 36/87; A61K 36/63; A61K 3/02; A61P 3/02
See application file for complete search history.

(56) References Cited

U.S. PATENT DOCUMENTS

2016/0136100 A1* 5/2016 Miller .................. A61K 9/4808
424/451

* cited by examiner

*Primary Examiner* — Sahar Javanmard
(74) *Attorney, Agent, or Firm* — Dan DeLaRosa

(57) ABSTRACT

A formulation comprising at least one ketogenic agent, at least one cannabinoid, at least one polyphenol, at least one phytonutrient, at least one dietary nutrient, at least one antioxidant, and at least one mineral, and mixtures and combinations thereof utilized for performance, cardiometabolic, cognitive, and women's health and wellness.

10 Claims, No Drawings

COMPOSITIONS WITH KETOGENIC AGENTS, CANNABINOIDS, PLANT-DERIVED SUBSTANCES AND MICRONUTRIENTS

FIELD OF THE INVENTION

The invention relates to the modulation of metabolic pathways to benefit human performance, endurance and cardiometabolic health while improving cognition and executive brain function and enhancing women's health. The invention utilizes high concentration ketogenic agent formulations including medium chain triglycerides (MCT), cannabinoids, dietary polyphenols, phytonutrients, other dietary nutrients, antioxidants and minerals to supplement the usual biochemical pathways which generate energy in the brain and body, provide cardiometabolic- and neuroprotection, and diminish adverse age-related health effects in women and improve general health.

SUMMARY OF THE INVENTION

The ingredient combinations are included because of their impact on broad aspects of human health as listed in the title of this invention. Polyphenols in particular demonstrate beneficial effect on performance parameters such as heart rate and blood pressure during exercise, oxygen consumption, peak power, nitric oxide levels, reaction time, balance and exercise capacity, reserve, tolerance and recovery. Cardio-metabolic factors, glucose and lipid profiles are also enhanced. Cholesterol, sugar and triglyceride levels are lowered while endothelial function, vascular reactivity and compliance are improved.

Antioxidants and carotenoids provide cognitive and neuroprotective qualities. Positively affected domains include working memory, concentration, conscious perception, focus, executive function, sustained attention and decision making. Additional findings support brain structure, visual processing, sleep patterns and neurogenesis (nerve cell growth).

Phytonutrients also are combined in the present formulation to improve various aspects of women's health and wellness. This approach extends beyond the hormonal issues that are usually the only factors considered in this situation. The areas shown in trials to be beneficially affected include cardiovascular, neurological and psychosocial. The latter include unpleasant symptoms such as depression, stress, anxiety, mood swings, night sweats and hot flashes. In addition, benefits are noted in issues of energy levels, weight control, bone health and libido and gratification.

The present invention provides for a comprehensive nutrient formulation comprising a novel combination of ketogenic agents such as natural MCT, coconut oil extracts and ketone salts/esters; pure "isolate" or "full spectrum" cannabinoids, such as cannabidiol (CBD) and tetrahydrocannabinol (THC); polyphenolic substances such as bergamot, chokeberry, curcumin, flavonoids, grape seed, olive leaf, spearmint and tea; phytonutrients such as damiana, maca and *Tribulus*; other dietary nutrients such as vitamins B3, B6, B9 (folate) and B12 and their precursors as well as carotenoids, choline and L-carnitine; antioxidants such as vitamins C and E, alpha lipoic acid, coenzyme Q-10 and N-acetyl cysteine; and minerals such as chromium, magnesium, selenium and zinc. A proprietary method of manufacture and flavoring comprising minimal ancillary ingredients including a flavor smoothing agent and naturally derived plant and fruit flavors and colors.

In one embodiment, the present invention relates to a formulation comprising at least one ketogenic agent, at least one cannabinoid, at least one polyphenol, at least one phytonutrient, at least one dietary nutrient, at least one antioxidant, and at least one mineral, and mixtures and combinations thereof.

In another embodiment, the ketogenic agent is selected from a group comprising MCT oil, ketone salts/esters, and coconut oil extracts, and mixtures and combinations thereof.

In yet another embodiment, the cannabinoid is selected from a group comprising cannabidiol, tetrahydrocannabinol, mixed cannibinoids, and mixtures and combinations thereof.

In still another embodiment, the polyphenol is selected from a group comprising bergamot, chokeberry, curcumin, flavonoids, grape seed, olive leaf, spearmint, tea, and mixtures and combinations thereof.

In yet another embodiment, the phytonutrient is selected from a group comprising Damiana, Maca, *Tribulus*, and mixtures and combinations thereof.

In still another embodiment, the dietary nutrient is selected from a group comprising Vitamin B3, Nicotinamide riboside, Vitamin B6, Vitamin B9, Vitamin B12, natural carotenes, lutein, Zeaxanthin, Choline, and L-carnitine, and mixtures and combinations thereof.

In yet another embodiment, the antioxidant is selected from a group comprising Vitamin C, Vitamin E, Alpha lipoic acid, Co-enzyme Q-10, N-acetyl cysteine, and mixtures and combinations thereof.

In still another embodiment, the mineral is selected from a group comprising Chromium, Magnesium, Selenium, and Zinc, and mixtures and combinations thereof.

In still a further embodiment, the ketogenic agents comprise 10 gms of MCT oil, 20 gms of ketone salts/esters, and 20 gms of coconut oil extracts.

In still yet another embodiment, the cannabinoids comprise 30 mg of cannabidiol, 15 mg of tetrahydrocannabinol, and 25 mg of mixed cannabinoids.

In another embodiment, the polyphenols comprise 1200 mg of bergamot, 300 mg of chokeberry, 500 mg of curcumin, 500 mg of flavonoids, 250 mg of grape seed, 200 mg of olive leaf, 900 mg of spearmint, and 500 mg of tea.

In yet another embodiment, the phytonutrients comprise 300 mg of Damiana, 250 mg of Maca, and 200 mg of *Tribulus*.

In a further embodiment, the dietary nutrients comprise 15 mg of Vitamin B3, 500 mg of Nicotinamide riboside, 3 mg of Vitamin B6, 600 mcg of Vitamin B9, 6 mcg of Vitamin B12, 15 mg of natural carotenes, 10 mg of lutein, 2 mg of Zeaxanthin, 125 mg of Choline, and 80 mg of L-carnitine.

In another embodiment, the antioxidants comprise 300 mg of Vitamin C, 90 IU of Vitamin E, 60 mg of Alpha lipoic acid, 45 mg of Co-enzyme Q-10, and 125 mg of N-acetyl cysteine.

In still a further embodiment, the minerals comprise 30 mcg of Chromium, 60 mg of Magnesium, 60 mcg of Selenium, and 9 mg of Zinc.

In still another embodiment, the formulation is used for performance, cardiometabolic, cognitive, and women's health and wellness.

In yet another embodiment, a formulation comprising:
MCT oil from about 1 gram to about 40 grams;
Ketone salts/esters from about 5 grams to about 40 grams;
Coconut oil extracts from about 1 gram to about 80 grams;
Cannabidiol from about 1 mg to about 800 mg;
Tetrahydrocannabinol from about 1 mg to about 800 mg;
Mixed cannabinoids from about 5 mg to about 1200 mg;

Bergamot from about 500 mg to about 1500 mg;
Chokeberry berry from about 50 mg to about 1,000 mg;
Curcumin from about 100 mg to about 1500 mg;
Flavonoids from about 100 mg to about 1200 mg;
Grape seed about 50 mg to about 500 mg;
Olive leaf from about 25 mg to about 400 mg;
Spearmint from about 500 mg to about 2000 mg;
Tea from about 25 mg to about 1000 mg;
Damiana from about 100 mg to about 600 mg;
Maca from about 50 mg to about 500 mg;
*Tribulus* from about 10 mg to about 400 mg;
Vitamin B3 from about 1 mg to about 35 mg;
Nicotinamide riboside from about 100 mg to about 2000 mg;
Vitamin B6 from about 1 mg to about 20 mg;
Vitamin B9 from about 100 mcg to about 1000 mcg;
Vitamin B12 from about 1 mcg to about 200 mcg;
Natural carotenes from about 1 mg to about 60 mg);
Lutein from about 6 mg to about 20 mg;
Zeaxanthin from about 0.1 mg to about 5 mg;
Choline from about 25 mg to 600 mg;
L-carnitine from about 25 mg to about 750 mg;
Vitamin C from about 50 mg to about 2000 mg;
Vitamin E from about 5 IU to about 400 IU;
Alpha lipoic acid from about 10 mg to about 150 mg;
Co-enzyme Q-10 from about 5 mg to about 120 mg;
N-acetyl cysteine from about 50 mg to about 500 mg;
Chromium from about 10 mcg to about 120 mcg;
Magnesium from about 25 mg to about 500 mg;
Selenium from about 10 mcg to about 150 mcg;
Zinc from about 1 mg to about 80 mg;
and mixtures and combinations thereof.

In a further embodiment, the present invention refers to a method of manufacturing a formulation, the method comprising admixing at least one ketogenic agent, at least one cannabinoid, at least one polyphenol, at least one phytonutrient, at least one dietary nutrient, at least one antioxidant, and at least one mineral, or any mixtures or combination thereof in varying amounts.

All categories of ingredients and ingredient sources herein are illustrative only and may include named ingredients, whether or not proprietary to the current invention, as well as alternative sources and iterations of such ingredients and ingredient categories, which may be substituted, added or may be novel to the present invention.

PRODUCT FORMULATIONS

This invention provides novel formulations for performance, cardiometabolic, cognitive and women's health that are derived from seven entirely separate categories of ingredients:
 a) Ketogenic agents
 b) Cannabinoids
 c) Polyphenols
 d) Phytonutrients
 e) Other dietary nutrients
 f) Antioxidants
 g) Minerals The combinations included in the standard formulation presented may vary within each category. Another unique enhancement to the present invention allows for targeted doses and broad dosage ranges to account for variations in bioavailability and individual consumer needs. Certain individuals may benefit from ingredient consumption that differs from the primary dose listed but is encompassed within the dose ranges. The higher ends of the ranges are generally intended for those who wish to address specific health issues or clinical symptoms. Supplementation may employ none of the ingredients from any particular category, all of the ingredients in a category or partial combinations from one or more categories. The doses listed are intended to be considered the total daily dose. For commercial application, this dosage may be consumed at one time or in multiple divided doses throughout the day.

The product platform for humans includes but is not limited to highly concentrated tinctures and oils in one half to two ounce sizes, less concentrated liquid beverage forms in two to two and one half ounce sizes; more dilute liquid beverage forms in eight to twenty ounce sizes; drops; powders; and multiple solid formats including pills, capsules, soft gels, tablets, bars, gummies, lozenges/troches, dissolvable disks, other edibles or chewables, patches, sticks; as well as aerosols, ointments, gels, and injectable, liposomal, microencapsulation, nanotechnology or other delivery systems. The standard risk formulation is intended for healthy consumers ages eighteen years and older.

Standard Risk Formulation

|  | Dosage: | |
| --- | --- | --- |
| Ketogenic Agents | Primary | Range |
| MCT oil (caprylic/capric acid) | 10 grams | (1-40 grams) |
| Ketone salts/esters | 20 grams | (5-40 grams) |
| Coconut oil extracts (caprylic, capric, lauric acid) | 20 grams | (1-80 grams) |

| Cannabinoids | | |
| --- | --- | --- |
| Cannabidiol (hemp-derived, full spectrum, pure isolate) | 30 mg | (1-800 mg) |
| Tetrahydrocannabinol (marijuana-derived, 0.3% or greater) | 15 mg | (1-800 mg) |
| Mixed cannabinoids (*Cannabis sativa* L-derived, distillate, crude) | 25 mg | (5-1200 mg) |

| Polyphenols | | |
| --- | --- | --- |
| Bergamot (*Citrus bergamia*, plant, berry, leaf, extract) | 1200 mg | (500-1500 mg) |
| Bergamot Polyphenolic Fraction - BPF | 47% | (30-55%) |
| Chokeberry (*Aronia melanocarpa*, extract, powder, capsules) | 300 mg | (50-1000 mg) |
| (juice concentrate) | 250 ml | (50-500 ml) |
| Curcumin (turmeric root) | 500 mg | (100-1500 mg) |
| (extract) | 180 mg | (50-500 mg) |
| Flavonoids (cocoa) | 500 mg | (100-1200 mg) |
| Grape seed (extract, stilbenes, resveratrol) | 250 mg | (50-500 mg) |
| Olive leaf (oleuropein, 10-30%) | 200 mg | (25-400 mg) |
| Spearmint (Neumentix ™ proprietary extract or other sources) | 900 mg | (500-2000 mg) |
| Tea (black, green, *Moringa*) | 500 mg | (25-1000 mg) |

| Phytonutrients | | |
| --- | --- | --- |
| Damiana (leaf, powder, 10-30%) | 300 mg | (100-600 mg) |
| Maca (root, gelatinized 20:1 extract, 0.6% macamides, macaenes) | 250 mg | (50-500 mg) |
| *Tribulus* (Bulgarian *terrestris*, Aerial extract, 40-50%) | 200 mg | (10-400 mg) |

| Other Dietary Nutrients | | |
| --- | --- | --- |
| Vitamin B3 (niacinamide ascorbate, yeast sources) | 15 mg | (1-35 mg) |
| Nicotinamide riboside (Niagen ®) nicotinamide adenine dinucleotide, or other sources, NAD+, NADH) | 500 mg | (100-2000 mg) |
| Vitamin B6 (pyridoxine hydrochloride, yeast sources) | 3 mg | (1-20 mg) |
| Vitamin B9 (folate, folic acid, folacin, yeast or liver sources) | 600 mcg | (100-1000 mcg) |
| Vitamin B12 (methylcobalamin, yeast sources) | 6 mcg | (1-200 mcg) |
| Carotenoids | | |
| Natural carotenes (alpha, beta, gamma, sea, algal, plant sources) | 15 mg | (1-60 mg) |
| Lutein FloraGLO ® proprietary extract or other sources) | 10 mg | (6-20 mg) |
| Zeaxanthin (FloraGLO ® proprietary extract or other sources) | 2 mg | (0.1-5 mg) |
| Choline (salts, citicoline, lecithin, phosphatidylcholine) | 125 mg | (25-600 mg) |
| L-carnitine (fumarate or natural forms) | 80 mg | (25-750 mg) |

| Antioxidants | | |
| --- | --- | --- |
| Vitamin C (ascorbate, ascorbic acid, citrus, rose, berry sources) | 300 mg | (50-2000 mg) |
| Vitamin E (wheat germ, vegetable sources, natural tocopherol) | | |
| (d-alpha tocopheryl succinate) | 60 IU | (30-400 IU) |
| (d-alpha tocopheryl acetate) | 30 IU | (5-200 IU) |
| Alpha lipoic acid (R+, R−, yeast or liver sources) | 60 mg | (10-150 mg) |
| Co-enzyme Q-10 (ubiquinone, natural sources: organ meat, *Paracoccus denitrificans*, *Agrobacterium tumefaciens*, *Pseudomonas aeruginosa*) | 45 mg | (5-120 mg) |
| N-acetyl cysteine (L-cysteine, natural sources: sesame/flax seeds, soy extracts, oat bran, wheat germ, Swiss cheese, peas, whole grains) | 125 mg | (50-500 mg) |

| Minerals | | |
| --- | --- | --- |
| Chromium (chloride, nicotinate, picolinate, citrate, yeast sources) | 30 mcg | (10-120 mcg) |
| Magnesium (citrate, lactate, gluconate, oxide, carbonate, hydroxide, lactic acid, chloride, sulphate, Jay phosphate, tribasic phosphate, natural forms) | 60 mg | (25-500 mg) |
| Selenium (L-selenomethionine, sodium selenite/selenite, natural forms) | 60 mcg | (10-150 mcg) |
| Zinc (glycinate, gluconate, oxide, sulphate, natural forms) | 9 mg | (1-80 mg) |

For commercial use, it is intended that this product formulation may contain the following ingredients per category:

a) at least one of the ingredients in the "Ketogenic Agents" category b) at least one of the ingredients in the "Cannabinoids" category c) at least one of the ingredients in the "Polyphenols" category d) use of ingredients in the "Phytonutrients" category is optional e) use of ingredients in the "Other Dietary Nutrients" category is optional f) use of ingredients in the "Antioxidants" category is optional use of ingredients in the "Minerals" category is optional Rationale for Components Ketogenic Agents The human brain functions energetically on only two sources of fuel, either primarily glucose or alternatively ketone bodies. The latter is an evolutionarily selected alternative source of energy in times of starvation, disease, stress or short supplies of food. To provide incremental "energy" to the brain and improve function with actual benefit to mitochondrial energy generation, the ketogenic agent must not be destroyed during intestinal digestion and be able to cross the blood brain barrier.

Cognitive performance diminishes with advancing age. Imaging studies have demonstrated that the brain suffers a gradual diminished capacity to process glucose resulting in a hypo-metabolic state. Neurons lose the ability to efficiently process glucose, become energy deprived, functionally decline and begin to undergo apoptosis or cellular death.

Normally, when the diet provides an adequate supply of carbohydrate, glucose is the fuel used by the brain. However, when the availability of dietary carbohydrate is significantly limited, ketone bodies such as hydroxybutyrate and acetoacetate produced in the liver provide alternative fuel for central nervous system neurons. Ketones are preferentially metabolized, when available, and used by the brain for energy.

In some neurological and metabolic conditions, including age-related cognitive impairment, the aging brain is unable to access or process glucose efficiently. When provided exogenously, ketones supply the necessary energy and restore the ability of fuel-depleted mitochondria in key brain cells to function normally. Thus, cognitive and memory functions that depend on mitochondria-generated processes can remain operant. Even should neuronal loss retard this restoration, the progression of neurodegeneration can be delayed.

Since MCT generated ketone bodies provide neurons with an alternative energy source to glucose, the cognitive improvement from MCT supplementation is positively correlated with blood levels of beta hydroxybutyrate. This organic compound resulting from ketogenesis after consumption of MCT, demonstrates that blood concentrations are elevated sufficiently to provide the brain with a reliable ancillary fuel source.

Ketones and Cognitive Performance.

Dietary MCT supplementation has concurrent long-lasting cognition enhancing effects. Age associated reduction in cerebral glucose metabolism is a common feature in diseases of older adults. The process involved is progressive and starts in early middle age or sooner. A ketogenic diet has been tested as a means for mitigating this further damage. It is a high fat content diet in which carbohydrates are nearly eliminated so that the body has minimal dietary sources of glucose. High rates of fatty acid oxidation occur and lead to the synthesis of ketone bodies from acetyl-CoA, mainly in the mitochondrial matrix of liver cells.

Plasma levels rise, with acetoacetate and β-hydroxybutyrate increasing three to four-fold or more from basal levels of 100 and 200 μM, respectively, providing an adequate energy source for brain tissue. However, for ideal neuroprotection, even higher levels of ketone bodies are necessary in the affected area of the brain. Oral ketone esters have been tried but have a very short half-life and serious potential side-effects as well as significant palatability and digestibility issues. This invention provides new methods for elevating cerebral ketone body concentration on a sustained basis.

Ketogenic Agent Source Options

This effective means of elevating the energetic metabolism of brain tissue is through introduction of supplementary ketogenic MCT (KMCT) beyond the naturally occurring levels in the human diet. The inventors discovered that KMCT achieves this elevation of ketone levels, when provided in proprietary formulations and manufactured with proprietary methods. KMCT are metabolized in the liver to provide a rich source of ketone bodies, which can be metabolized as a carbon and energy source for the body, especially the brain. Unlike ketogenic dieting, providing exogenous KMCT does not result in reduced glucose concentrations or other adverse physiological effects and does not suffer from patient compliance issues. Ingestion of KMCT has no reported serious side effects and only minor, transitory gastro-intestinal distress or sensitivity in some individuals. Among others, one source option for such KMCT is Fuel for Thought® (Ultimate Brain Nutrients, LLC) an orally bioavailable nutritional supplement comprising primarily caprylic triglycerides, together with additional ingredients as described herein.

Ketone Bodies, Esters, Salts

Ketone bodies generated in the liver from fatty acids are a potential energy source for the human body, with particular affinity and efficacy in brain and heart tissue. Increasing the blood level of ketone bodies directly improves both cognitive and physical performance. The ketone bodies, hydroxybutyrate and acetoacetate, can be consumed to elevate ketone levels. However, the direct consumption of these compounds is difficult and potentially hazardous since it may cause acidosis, a clinically relevant metabolic disorder.

Ketone esters can, however, be more safely consumed in combination with other compounds as proposed in the present application. In addition, the salts of beta-hydroxybutyrate taken with MCT will induce ketosis, resulting in improvements in clinical parameters for insulin resistance or diabetes as well as physical performance and weight management. Through sophisticated flavor chemistry the inventors have addressed the problem of intrinsic taste and palatability difficulties of oral administration of ketones.

The present invention will utilize ketone esters and salts in varying formulas, as individual additives and in combinations and racemic mixtures. As noted, ingredient sources may vary.

Coconut Oil Extracts (Caprylic, Capric, Lauric Acid)

The direct ingestion of coconut oil has ketogenic activity, due to the presence of MCT. The MCTs in coconut oil are generally easily digested, converted in the liver to ketones, beneficial to brain activity and may have thermogenic fat burning effects. Another triglyceride, lauric acid decreases levels of the hormone Ghrelin, reducing hunger.

Coconut oils contain approximately 60% MCT (composed of 48% lauric acid, 6.8% caprylic acid and 6.6% capric acid). Laurie acid converts to monolaurin in the human body which can act as an antiviral, while capric and caprylic acids may be antimicrobial lipids. Coconut oil and its constituent MCT improves the body's use of insulin, improves cholesterol profiles by increasing high density lipoprotein ("good" cholesterol), may positively affect thyroid function and reduce the excess free radical-induced oxidative damage implicated in chronic diseases.

The quality of coconut oil is essential to its function. This invention avoids lower grade or undisclosed quality coconut oil ingredients that are extracted with solvents or refined, bleached and deodorized. The inventors incorporate only whole coconut oil as well as responsibly produced extracts of coconut oil into the final product formulation. It will also utilize only the highest value cold, expeller-pressed coconut oil, containing no solvents which may impair or negate the beneficial effects of the ingredients.

Cannabinoids

An important human physiologic regulatory system is the endocannabinoid complex which comprises endogenous lipid-based neurotransmitters which bind to cannabinoid receptors, throughout the brain and peripheral nervous systems. The endocannabinoid system is a naturally forming system that regulates a wide variety of physiological processes, such as mood, memory, and appetite. Additional physiological and cognitive activities include pain-perception, emotional states, aspects of cognition and memory, appetite regulation, and fertility, pregnancy and postnatal development. Endocannabinoids are also instrumental in mediation of voluntary physical exercise. These include the satisfaction response and locomotor regulatory effects of such activities. In humans, the plasma concentration of certain endocannabinoids have been demonstrated to increase during physical activity. Endocannabinoids penetrate the blood-brain barrier, and may tangibly contribute to the "so called runner's high".

There are at least 113 different cannabinoids that have been isolated from the *Cannabis* plant. Of these more than a hundred phyto-cannabinoid constituents of the terrestrial plant, *Cannabis sativa* L. (innaeus), the most scientifically evaluated and relevant are cannabidiol (CBD) and tetrahydrocannabinol (THC). The common name hemp is defined as species of *Cannabis sativa* L. that contain less than 0.3% of the psychoactive ingredient THC. Marijuana is classified as species that contain 0.3% or greater THC. In the native forms, both hemp and marijuana contain CBD and THC. Hemp contains higher concentrations of CBD and lower concentrations of THC while marijuana contains reciprocal concentrations of these major components. Hemp oils, proteins and extracts from the plant leaves, seeds or fibers provide CBD-rich product concentrations that can be processed into nutritional consumables for oral (solid or liquid) ingestion, smoking (or vaping) inhalation, topical absorption or even parenteral (injectable) applications.

The non-psychotropic cannabinoid, CBD, has demonstrated various health benefits and the potential for several more. This invention provides options of "pure" forms of CBD and the method of manufacture maximizes this high concentration of active ingredient. One form is the "isolate" crystalline product or powdered form that contains essentially all CBD. Its effectiveness can be maximized employing a micro-encapsulation technique in a water-soluble format. The second form is "full spectrum" or whole plant CBD that also contains small amounts of other cannabinoids. Most importantly, it contains only trace (less than 0.3%) amounts of THC, that has essentially a minimal psychoactive effect if any at all. Alternative forms not utilized in this invention include a "distillate" with a high concentration oil that contains 50-85% CBD together with other cannabinoids including THC. There is also a "crude" extract that contains various components including many cannabinoids, oils, terpenes and chlorophylls.

In addition, this invention will take advantage of any future legal status for cannabinoid-containing supplement mixtures. This should potentially allow the public to access the proven health benefits of cannabinoids. While initial reports were anecdotal medical observations, an increasing number of in vitro, animal and human studies have demonstrated clinical therapeutic effects. Cannabinoids can act as antidepressants as well as relaxation agents against anxiety and stress disorders. Demonstrated mechanisms of action include effects as anticonvulsants (seizures), antiemetics (nausea and vomiting), analgesics (pain) and anti-inflammatory agents. This class of products also provides antioxidant effects, neuroprotection and may reduce the adverse effects of excessive smoking and alcohol intake.

In vivo animal research has documented mechanisms of action including antioxidant effect against excess free radical-induced oxidative damage, potential protection against neurodegenerative conditions such as Parkinson's disease, reduction of stress-related pain and anti-inflammatory responses in asthma models. Individual case reports also document benefit in clinical psychoses, childhood seizures, social anxiety, marijuana addiction and post-traumatic stress disorder. Novel applications of cannabinoids include such as inhibition of carcinogenesis, toxic glutamate neurotransmission and seizure-related brain damage while providing potential therapy for lung diseases.

Human clinical trials of cannabinoids showed relaxation with diminished stress and anxiety as well as improvement in waking and sleep patterns in healthy subjects. Unique combinations of these compounds lower plasma alcohol levels and reduce the anxiety and feeling of intoxication from marijuana use. In addition, increase in sleep duration in insomniacs and improved seizure symptoms in treatment-refractory epilepsy patients is noted. In subjects with social anxiety disorder, cannabinoids reduce anxiety, cognitive impairment and speech performance discomfort while improving regional blood flow to the brain. There is also a positive impact on psychotic symptoms in acute schizophrenia patients. In patients with pain from multiple sclerosis, neurogenic causes or cancer, different dosage combinations demonstrate some beneficial effects.

It must be noted that bioavailability of cannabinoids varies greatly with method of use, this invention takes advantage of adequate target doses for healthy individuals with wide dosage ranges to account for different clinical situations and various delivery platforms. Oral consumption generally delivers 5-20% absorption into the blood stream while oral mucosal (under the tongue) absorption may provide up to double this amount. Inhalational (vaporizing) methods probably afford the highest bioavailability, in the 35-50% range. Several platforms may be utilized in the present invention to provide clinically effective dosages for the desired spectrum of symptoms. These include various beverages, oral formats for oils, sprays, tinctures, chewables (gummies and lozenges) and other edibles, as well as lotions and creams for topical application, inhalational oils for vaping and fragrance products such as body powders and candles. The anti-inflammatory attributes of cannabinoids can also be combined with effective phytonutrient and micronutrient formulations for metabolic syndrome, diabetes, heart disease or neurological conditions.

Polyphenols

Micronutrients derived from plant-based foods. They are packed with antioxidants and have health benefits.

Bergamot

The bergamot plant (*Citrus Bergamia* Risso) originated in the Calabria region of southern Italy. The health benefits of bergamot and other citrus fruits present a broad spectrum of effects including not only as antioxidants but also as modulators of enzymes, receptors, genes and cell signaling pathways. Bergamot polyphenol fraction (BPF) is the potent extract derivative of the fruit juice and pulp that contains the active catecholic flavonoids. The metabolic activities are related to the particularly high content of polyphenols, flavonoids and other bioactive compounds such as rutin within bergamot species. The plant's polyphenolic fraction has been characterized with the highest concentrations as utilized in the present invention being the most efficacious. Effects include kinase enzyme regulation, and energy production while promoting glucose uptake and fat metabolism. BPF also imparts cardio-metabolic benefits in human studies such as improvements in cholesterol and lipid particle profiles. To enhance active performance and recovery, BPF increases stamina and oxygen uptake, protects heart rate during exertion and improves vascular function. Citrus flavonoids can also demonstrate several mechanisms to provide anti-inflammatory and neuroprotective properties.

Chokeberry

In a similar manner as with the bergamot plant, the chokeberry shrub also contains a variety of polyphenol constituents, anthocyanins and procyanidins that account for the many beneficial biological effects that can be demonstrated in the laboratory as well as in vivo and in human trials. This well-characterized phytonutrient has been compared to many other fruit plants and has been found to contain among the highest levels of phenolic content and antioxidant activity. Further research has shown that Aronia fruit extracts may protect vascular endothelial cells from oxidative stress-related dysfunction thereby potentially diminishing the progression of coronary artery disease. In addition, many fruit extracts are known to inhibit the growth of cancer cells. However, Aronia's activity has demonstrated among the strongest effects in this regard. Finally, chokeberry juice may provide a potent anti-diabetic effect in relation to reduction in weight and blood glucose levels.

Curcumin

Curcumin is a phytonutrient abundantly present in the spice, turmeric, and demonstrates a wide spectrum of therapeutic properties. Its potential application to lung protection from hazardous exposures has been described. Immune enhancement is another potential benefit. This polyphenolic agent decreases muscular pain and reduces inflammation and post-exercise muscle damage in human subjects. It improves in vivo neural functioning and protects against oxidative stress and brain ischemia-reperfusion injury. Curcumin has also shown benefit against oxidative damage, and in combination with resveratrol, demonstrates unique radioprotective qualities on normal tissues. Relative to this invention, the characteristics of the nutrient are important for active performance and neurocognitive health status.

Grape Extracts

Grape seeds and extracts thereof protect against ultraviolet radiation via their phenolic compounds, the proanthocyanidins. Grape juice polyphenols and resveratrol improve antioxidant capacity and diminish oxidative stress. These compounds protect neurocognitive function in older adults and spatial memory and performance in younger adults. Resveratrol is a polyphenolic compound derived from the skin of grapes and other berries and is also neuroprotective as a single agent. It has importance in environmental exposure as shown by its protective effect against the oxidative stress caused by cigarette smoke. In addition, there are number of studies that document its protective antioxidant effect against radiation damage.

Olive Leaf

Olive tree leaves are an important source of concentrated polyphenolic compounds and flavonoids. The primary active substance is oleuropein and is present in higher amounts per volume in the leaf than in extra virgin olive oil. As with other plant-based nutrients, selective methods of extraction yielding high polyphenol levels may account for the reported health benefits. Olive leaf extracts are utilized to provide protection against hostile environmental factors as well as demonstrating broad antioxidant properties.

Spearmint

The mint (genus *Mentha*) plant of the Lamiaceae family is well known to contain many active phytochemicals. Among the species of mint, the spearmint (*Mentha spicata* L.) exhibits a variety of important and potential clinically relevant properties because of its broad component profile. This includes active polyphenolic compounds such as rosmarinic acid, salvionolic acid, caftaric acid and lithospermic acid. Spearmint leaves, oils and aqueous and phenolic extracts have demonstrated a robust safety record in experimental and in vivo studies. These derivatives of the plant have been granted GRAS (generally recognized as safe) status in the United States.

This plant-based, high polyphenol-containing nutrient has demonstrated a variety of cognitive benefits in human clinical trials. The mechanisms of action include reduction in oxidative stress, support of neurotransmission, neurogenic induction and neuroprotection. The beneficial effects include aspects of cognition, sleep support and physical performance. Studies have shown improvement in working memory, short term memory, concentration, focus, sustained attention, falling asleep faster and support of physical multitasking, agility and reaction time.

In vitro testing has demonstrated free radical scavenging, decreased lipid peroxidation in the brain and attenuation of reactive oxygen species. Animal studies showed reduction of oxidative damage in the cerebral cortex and hippocampus. It is known that the neurotransmitter, acetylcholine, strengthens neural pathways in the brain. Importantly, the components in this phytonutrient consistently decreased cholinesterase in in vitro and in vivo experiments. Neuroprotection has also been demonstrated by downregulating apoptosis in cell line and animal studies as well as by decreasing neuronal loss and protecting mitochondrial membrane potential. In vitro studies have shown broad antioxidant properties. These findings were confirmed in animal models. In vivo studies have also been utilized to demonstrate anti-apoptotic activity and benefit to neuronal cell health. Of clinical potential is the neurogenic and neuroprotective qualities of spearmint polyphenols. Specific studies of neurological disease show important findings such as protection of memory in amyloid peptide-induced Alzheimer's models. Likewise, similar neuroprotection in models of Parkinson's disease has been shown. In addition, spearmint compounds provide beneficial effects in brain function, oxidative damage and inflammation in murine models. Finally, a human clinical trial has confirmed in vivo findings in relation to improvement in cognitive function.

Laboratory analyses have confirmed high plasma levels of the key active phenolic molecules and their metabolites. Human clinical trials in older individuals have proven clinical benefits in cognitive domains such as working memory as well as better sleep patterns. A trial in young subjects demonstrated benefit in reactive agility on a task requiring hand and foot movements along with enhanced sustained attention.

Spearmint Source Options.

It is critical that the plant-based extract that is selected for this invention contains an effective concentration of the key polyphenolic compounds. Among other sources, a dried aqueous acidic extract is available that is prepared from two proprietary non-genetically modified lines of *Mentha spicata* L. The complex produces higher concentrations of phenolic molecules than what is commercially available. This optional product is Neumentix™ (Kemin Foods L.C.) that contains a combination of polyphenols including rosmarinic, salvianolic A, salvianolic B, lithospermic and caftaric acids. The method of manufacture utilizes rhizome transplanting, a technique that maintains plant clonality to enhance production.

Tea (Black, Green, Moringa)

Black and green tea beverages show strong antioxidant effects in human trials and in vitro protection against radiation exposure. It has also been suggested that green tea in combination with Gingko biloba may provide substantial photoprotection. Extracts of black and green tea, including the compound theanine, have neuroprotective qualities. These components prevent memory impairment and improve cognitive function in humans of varying age as well as showing promising effects in psychiatric and neurodegenerative disorders.

A widely utilized edible plant, Moringa oleifera, has provided beneficial human nutritional supplementation in a variety of forms including leaves, seeds, flowers, roots, oils, bark, sap, gum and pods. Whole plant forms or aqueous and ethanol extracts of this phytonutrient have been prepared with multiple modes of delivery usually by oral consumption of teas, powders or tablets. Administration of whole plant forms has been shown to be safe in animal studies up to doses of 2000 mg/kg, and in human trials up to doses of 500 mg/kg. Extracts show no in vivo toxicity in doses up to 100 mg/kg.

In vitro and animal studies have shown protective biological activity of Moringa as an antioxidant, anti-lipidemic, antidiabetic and anti-inflammatory agent. The plant also has demonstrated gastrointestinal and hepatoprotective characteristics in experimental models. Of further interest are the neuroprotective qualities of this nutrient in terms of cerebral ischemia, memory impairment and anxiety disorders. Moringa has also been shown to have significant in vitro anti-cancer effects. Human studies have confirmed antioxidant, anti-hyperglycemic and anti-lipidemic properties without any toxicity.

Phytonutrients

This category of adjunctive ingredients included in some versions of the present invention has been analyzed in human performance studies and women's health clinical trials. Results have been positive in a spectrum of parameters in recreational athletes. In addition, biological effects have been demonstrated in women relative to mood, energy and hot flashes as well as psychosexual factors and bone health. Three plant-based products comprise this optional category of adjunctive supplements.

Damiana

The shrub, damiana (*Turnera diffusa*) is common in many regions of North and South America. Damiana appears to derive the reported beneficial properties from its carotenoids, polyphenols, flavonoids and fatty acids. Specifically, in relation to women's health, this phytonutrient's effects have been demonstrated in anxiety states as well as for depression, blood sugar and weight control.

Maca

The maca plant (*Lepidium meyenii*) is also known as Peruvian ginseng because of its origins in the Andes mountains of Peru. The maca root is most commonly consumed and is available in the form powder, gelatin or extracts. The phytonutrient composition is complex and provides anthocyanins, amino acids, proteins, dietary fiber, fatty acids, carbohydrates and minerals. Recent studies have demonstrated potential beneficial endocannabinoid-like properties. Although trials are limited, there are reported effects in women include reduction of stress, anxiety and some menopausal symptoms and mood elevation.

Tribulus

This leafy plant (*Tribulus terrestris*) is widely grown in Europe, Asia and Africa. Also known as Bulgarian *Tribulus*, the phytonutrient has shown some positive cardiometabolic and hormonal/sexual effects in animal models as well as in men and women. The beneficial characteristics are thought most likely to be related to the plant's antioxidant properties and to the fact that it contains steroidal saponins that act as immune modulating chemicals in humans.

Other Dietary Nutrients

Vitamin B3

The complex referred to as vitamin B3 comprises niacin, niacinamide and nicotinamide riboside (NR). These forms all produce the compound, nicotinamide adenine dinucleotide (NAD), that is critical for human metabolism, cellular function, transfer reactions and DNA repair. NR is particularly effective for this purpose. NAD is a requisite in enabling cells to produce energy in the mitochondria and works synergistically with other energy sources such as ketones. It is also an important substrate for NAD-consuming enzymes including the sirtuins, that have potential beneficial effects on aging and circadian rhythms, and poly ADP-ribose polymerases, a family of proteins involved in essential cellular functions including genomic stability, DNA repair and programmed cell death, or apoptosis.

Extensive research studies show that NAD levels decrease with advancing age and under metabolic stress. Supplementation of NR has been demonstrated to help support many aspects of healthy aging, including cardiovascular and brain health. It also helps generate energy in mitochondrial-dense tissues like muscle, brain, and liver. NR has achieved GRAS (generally recognized as safe) status in the United States as a food ingredient in nutritional products. The present invention includes NR as an optional adjunctive ingredient for further energy and performance support. Among others, one available credible product to provide the necessary NAD effect has been found in Tru Niagen™ (Chromadex Corporation).

Vitamin B6

The most important functions of vitamin B6, pyridoxine, are related to the health of the nervous and immune systems. Specifically, this vitamin is involved in the biosynthesis of neurotransmitters thereby impacting cognitive development. Deficiency is associated with several clinical conditions resulting in low plasma concentrations. While adequate levels have not definitively shown effect in cancer or cardiovascular disease, there appear to be health benefits in neurocognitive domains.

Vitamin B9

Folate and its folic acid form are critical in the synthesis of nucleic acids and amino acid metabolism through its function as a coenzyme. Deficiency is generally related to inadequate food or supplement intake and is represented by a wide spectrum of symptoms. Folate deficits are associated with bowel cancer risk and supplementation may reduce this. Similar to other B vitamins, folate's effect in heart disease is inconsistent but may be protective against vascular-related ischemic stroke. In addition, several studies have shown benefit in individuals with depression. These findings have particular relevance in the broad health platform of this invention.

Vitamin B12

Vitamin B12 is a water-soluble vitamin that is necessary for neurological function, DNA synthesis and red cell formation as well as acting as an important enzymatic co-factor. As with other B vitamins, deficiency syndromes can show a wide spectrum of symptoms. Older individuals are especially affected. Because of its cognitive effects, vitamin B12 continues to be assessed in dementias. While there is data suggesting that the commonly used cyanocobalamin form may be implicated in kidney dysfunction, methylcobalamin is an alternative safe form for supplementation of the vitamin.

Carotenoids

Beta carotene usually as part of a natural mixed carotenoid source is a precursor to vitamin A and an essential antioxidant that decreases excess free radical-induced oxidative damage. Beta carotene uniquely increases the expression of the connexin gene that encodes for a gap junction protein that is necessary in maintaining normal cellular phenotypes. Along with related carotenoids, it is also effective in quenching oxygen-derived free radicals and protects cellular components in lipid environments. Only the natural isoforms demonstrate the ability to reduce these cellular abnormalities.

These naturally occurring organic pigments accumulate in many body tissues such as the brain and comprise prevalent and strongly active antioxidants in the cerebral cortex and brain stem structures, including the hippocampus and the macula of the eye. Emerging research has documented the role of carotenoids in promoting broad cognitive health and vision protection. In addition to natural mixed carotenoids, there are two others of importance that are orally consumable in the diet or through supplementation. These are the xanthophyllic antioxidants, lutein and zeaxanthin. Lutein independently demonstrates antioxidant properties in humans with related health benefits. It reduces oxidative stress in individuals with low antioxidant status subjected to hostile environments. This substance has a unique characteristic in that it can induce increases in physical activity in sedentary persons and is also neuroprotective against transient brain ischemia.

The carotenoids employed in the present invention are known to effectively cross the blood brain barrier and are preferentially accumulated in the brain. The high metabolic rate that occurs in the central nervous system makes the brain particularly susceptible to oxidative stress. Lutein and zeaxanthin specifically function in this regard as powerful antioxidants and protect the brain from free radical damage as well as support normal function and structure. These neuroprotective benefits have been proven in human studies. Randomized clinical trials found improved cognition in the areas of complex attention, reasoning and spatial memory as well as increased cortical activity detected on functional MRI scanning. Further investigations showed protection of the retina of the eye against harmful blue light, oxidative damage and macular degeneration. Finally, a study in older subjects led to improved cognition in regard to complex attention and cognitive flexibility.

Carotenoid Source Options

As with the other components of this invention, the most credible and effective carotenoid sources are critical to the uniqueness of the ultimate formulation. As noted, only natural isoforms of carotenoids are effective in cellular protection and a mixed carotene source would obviate any perceived problems associated with "pure" beta carotene supplements. Also necessary are high purity concentrations of lutein and zeaxanthin that can demonstrate accumulation in the eye as detected by "macular pigment optical density" testing. This measurement is valuable since it is strongly correlated with tissue levels of the active nutrients in the brain. Among others, one product to provide the necessary antioxidant effect has been found in FloraGLO Lutein® (Kemin Foods, L.C.). This complex is derived from a proprietary hybrid of the marigold plant and contains a consistent concentration of zeaxanthin at 0.83 mg for each 10 mg of lutein. Supplementation provides a sustained more than doubling of the plasma lutein levels. The robust product stability maintains tissue content for months. A U.S. patent documents the formulation's protection against the potentially harmful exposure from sunlight, computers and smart phone screens. This carotenoid combination has been widely researched and has a 25-year public safety record. It was utilized and proved beneficial in the landmark eye health supplement trial, AREDS2, conducted by the U.S. Government's National Eye Institute.

Choline

This essential nutrient is critical in humans because it is the precursor of acetylcholine, a neurotransmitter that is central to many bodily processes including muscular action, cognitive function and memory. It has been recognized as an "essential" substance by the U.S. Food and Nutrition Board for more than 20 years. Choline also contributes to cell signaling and structural integrity while its deficiency is implicated in atherosclerosis, liver disease and neurological disorders. Although it is available from dietary sources, supplementation may still be useful and official daily Adequate Intake values have been published.

L-carnitine

Only the natural "L" form of (acetyl-, proprionyl-) L-carnitine is biologically active in humans. This agent is included in the invention because of its role in performance, inflammation, pain, oxidative stress and neuroprotection. L-carnitine also shows beneficial effects in lipid metabolism and potentially in diabetes and obesity. It is safe and well-tolerated for extended time periods and the crosses the blood brain barrier. Various forms have demonstrated positive clinical benefits in vascular and neurodegenerative conditions. It can also protect against radiation-induced sensory organ and brain damage. In addition, L-carnitine and alpha lipoic acid synergistically enhance mitochondrial function.

Vitamins C and E

Vitamin C prevents lipid oxidation and potentiates nitric oxide activity in normalizing vascular function in patients with cardiovascular disease associated with high blood pressure, high cholesterol levels and in smokers. Vitamin C also plays an important role in maintaining cellular levels of vitamin E by recycling the vitamin E radical (oxidized) to the reduced (antioxidant) form. Mutations in the metabolic and genetic cellular mechanisms in hematopoietic stem cells can lead to blood cancers. Vitamin C appears to restore normal cellular regulation and may reduce cancer risk and suppress cancer progression. Vitamin C as calcium ascorbate is an effective non-acidic form available for human use and is less likely to cause stomach upset, diarrhea, and other issues that may affect some individuals consuming the ascorbic acid form of the vitamin.

Vitamin E is a robust antioxidant that reduces oxidation of membrane and LDL cholesterol, reduces c-myc activated pathways responsible for smooth muscle cell proliferation and reduces aggregation of platelets. The proper form, ratio and type of vitamin E are important since not all forms are easily soluble and can enter cells. Human tissues selectively absorb the natural form of vitamin E, d-alpha tocopherol, which acts in the intestinal tract and in the extracellular space. It stimulates the immune system whereas other forms of tocopherol (e.g. beta, gamma, delta) do not. The d-alpha tocopheryl succinate form of vitamin E is the most effective natural form of this micronutrient to maintain internal cellular components and it also actively reduces the incidence of radiation-induced transformation.

Employing multiple antioxidants together is usually most effective. A combination of antioxidants is more effective in tumor cell growth inhibition than any individual agents. Vitamin C and vitamin E are synergistic against free radicals because they protect both the aqueous and lipid environments of the cells respectively. They also produce a synergistic inhibition on LDL-cholesterol oxidation. These vitamins and beta-carotene have also been shown to be effective radio-protectants. Additional antioxidant combinations can protect against ischemia and reperfusion injury. It is also recognized that oxygen level may vary widely within the organs, tissues and individual cells. This is especially true during the biological damage related to the many adverse health factors addressed by this invention. Carotenoids act more effectively as antioxidants in high oxygen environments, whereas vitamin E is a more effective antioxidant at reduced oxygen pressures.

Endogenous Antioxidants

Glutathione, a sulfhydryl compound, is the body's primary endogenously formed antioxidant. It can catabolize anions and hydrogen peroxide and is a potent intracellular protective agent against excess free radical damage. In addition, reduced glutathione actively protects both normal and cancer cells against radiation damage. Specifically, sulfhydryl compounds protect against radiation injury to the bone marrow and gastrointestinal system as well as against cellular mutagenesis and can induce radiation resistance. However, when glutathione is consumed by humans, its plasma levels do not significantly increase suggesting that this tripeptide is completely hydrolyzed in the intestinal tract during digestion.

N-Acetyl Cysteine and Alpha Lipoic Acid

Therefore, two effective endogenous agents have been utilized in the present invention. N-acetylcysteine and alpha lipoic acid have been shown to actively increase intracellular glutathione levels by different non-competing mechanisms. They are well tolerated in humans, are rapidly absorbed without toxicity and have demonstrated radio-protective value. This further confirms their antioxidant value since it is estimated that most of the cellular damage from radiation is due to excess free radicals. These agents also restore glutathione in endothelial cells and cardiac muscle that suffered oxidative damage with resultant beneficial effects. Alpha-lipoic acid also has some unique functions in relation to metabolic disorders. It improves glucose utilization in peripheral tissue by stimulating glucose transport and uptake, thereby diminishing insulin resistance and decrease-related complications by reducing protein glycation and oxidative stress.

Co-Enzyme Q-10

Another optional adjunctive agent in this formulation is co-enzyme Q-10 (CoQ10), or ubiquinone. CoQ10 has demonstrated antioxidant properties albeit less potent ones than with the substances previously described. A fat-soluble compound, it is relevant to this invention because it assists in generating energy primarily in the mitochondria of the liver, heart and kidneys. CoQ10 is active in electron transport mechanisms and cellular oxygen uptake. Its free radical-scavenging qualities are likely responsible for some of the reported beneficial effects with various cardiovascular symptoms and neurological conditions.

Minerals
Chromium

This chemical element is considered an essential nutrient by the U.S. Food and Nutrition Board. One of the major biological properties is the effect on insulin regulation that is vital to protein, fat and carbohydrate metabolism. These factors likely account for some of the reported findings relative to pre-diabetes, weight control, fat storage and performance. A Recommended Daily Allowance has been published.

Magnesium

Magnesium holds a prominent position among essential elements that function as required co-factors for critical enzymatic reactions, biochemical function and metabolic pathways. Its supplementation is generally safe and is an effective therapeutic intervention in many clinical situations. It may also have a role as an electrolyte, has beneficial laxative properties and this mineral has been shown to be beneficial by extensive analysis of human clinical trials in modulation of pain perception inclusive of severe headache. In addition, magnesium supplementation has further demonstrated its broad applications having been reported to provide preventive symptom effects and reduce complications in surgical conditions.

Selenium

Selenium is a co-factor of glutathione peroxidase, and Se-glutathione peroxidase also acts as an antioxidant. This mineral also decreases harmful effects of pro-inflammatory cytokines and is radio-protective. Recent experimental studies have shown that selenium may protect against DNA damage and inhibit tumor progression. Therefore, selenium supplementation at adequate but safe doses is essential for promoting antioxidant enzyme systems and reducing potential oxidative stress.

Zinc

As has been noted in the present invention, trace elements play an important role in human health. Zinc is an essential micronutrient in this regard and functions as a biological catalyst and regulator with critical effects in oxidative stress, immune function, cellular integrity and the aging process. In fact, since zinc levels decline with age, there are broad international efforts to ascertain appropriate supplementation guidelines. In this population, zinc is vital to maintenance of DNA repair and genomic stability. Zinc also provides a protective antioxidant function against peripheral neuropathy in diabetic animal models. Several chronic diseases related to oxidative stress and inflammation are associated with inadequate zinc levels.

IMPACT OF THE INVENTION

The invention comprises administering to an individual an amount of ketogenic agent(s), cannabinoid(s) and polyphenolic compound(s) to enhance performance, cardiometabolic, cognitive and/or women's health issues. Adjunctive ingredients may include phytonutrients, antioxidants, minerals and/or other dietary nutrients.

In the case of ketogenic agents, this invention will employ one or more precursor of ketone bodies, in the form of MCT's, sufficient to raise the extracellular cerebral concentration of ketone bodies to at least about 1 to 10 mM. In some embodiments, the precursor is a medium chain triglyceride. In some embodiments, the precursor may itself be esterified to ketone bodies. In some embodiments, the precursor may be used in combination with a ketogenic diet.

In the case of cannabinoids, the present invention will employ a composition of agents that favors hemp-derived CBD over marijuana-derived THC. Appropriate concentrations of cannabinoids will be provided depending on the health targets of the consuming individual and the product platform method of consumption being utilized.

The dosages and dose ranges in this invention have been formulated for wide applicability and to account for the fact that less than 100% of these nutrient supplements are generally absorbed. Therefore, each ingredient category has been constructed to provide rational usage discretion and dose flexibility. The primary doses and ranges are designed to be at adequately broad and sufficient levels to impart the desired beneficial effects on performance, cardiometabolic, cognitive and women's health in humans of a wide range of ages and weights. The cited research demonstrates that the nutrient categories to which the components of the present invention belong are known to enhance performance, energy, psychological, cardiometabolic, cognitive and women's health domains as well as address a spectrum of symptoms, reduce oxidative damage, provide neuroprotection and, thereby, improve overall health status.

What is claimed is:

1. A formulation consisting of at least one ketogenic agent, at least one cannabinoid, at least one polyphenol, at least one phytonutrient, at least one dietary nutrient, at least one antioxidant, and at least one mineral, and mixtures and combinations thereof, wherein said formulation is admixed prior to being administered to an individual in a single medium, wherein said at least one ketogenic agent is selected from a group consisting of MCT oil, ketone salts/esters, and coconut oil extracts, and mixtures and combinations thereof, said at least one cannabinoid is selected from a group consisting of cannabidiol, tetrahydrocannabinol, mixed cannibinoids, and mixtures and combinations thereof, said at least one polyphenol is selected from a group consisting of bergamot, chokeberry, curcumin, flavonoids, grape seed, olive leaf, spearmint, tea, and mixtures and combinations thereof, said at least one phytonutrient is selected from a group consisting of Damiana, Maca, *Tribulus*, and mixtures and combinations thereof, said at least one dietary nutrient is selected from a group consisting of Vitamin B3, Nicotinamide riboside, Vitamin B6, Vitamin B9, Vitamin B12, natural carotenes, lutein, Zeaxanthin, Choline, and L-carnitine, and mixtures and combinations thereof, said at least one antioxidant is selected from a group consisting of Vitamin C, Vitamin E, Alpha lipoic acid, Co-enzyme Q-10, N-acetyl cysteine, and mixtures and combinations thereof, and said at least one mineral is selected from a group consisting of Chromium, Magnesium, Selenium, and Zinc, and mixtures and combinations thereof.

2. The formulation of claim 1 wherein said ketogenic agents consist of 10 gms of MCT oil, 20 gms of ketone salts/esters, and 20 gms of coconut oil extracts.

3. The formulation of claim 1 wherein said cannabinoids consist of 30 mg of cannabidiol, 15 mg of tetrahydrocannabinol, and 25 mg of mixed cannabinoids.

4. The formulation of claim 1 wherein said polyphenols consist of 1200 mg of bergamot, 300 mg of chokeberry, 500 mg of curcumin, 500 mg of flavonoids, 250 mg of grape seed, 200 mg of olive leaf, 900 mg of spearmint, and 500 mg of tea.

5. The formulation of claim 1 wherein said phytonutrients consist of 300 mg of Damiana, 250 mg of Maca, and 200 mg of *Tribulus*.

6. The formulation of claim 1 wherein said dietary nutrients consist of 15 mg of Vitamin B3, 500 mg of Nicotinamide riboside, 3 mg of Vitamin B6, 600 mcg of Vitamin B9, 6 mcg of Vitamin B12, 15 mg of natural carotenes, 10 mg of lutein, 2 mg of Zeaxanthin, 125 mg of Choline, and 80 mg of L-carnitine.

7. The formulation of claim 1 wherein said antioxidants consist of 300 mg of Vitamin C, 90 IU of Vitamin E, 60 mg of Alpha lipoic acid, 45 mg of Co-enzyme Q-10, and 125 mg of N-acetyl cysteine.

8. The formulation of claim 1 wherein said minerals consist of 30 mcg of Chromium, 60 mg of Magnesium, 60 mcg of Selenium, and 9 mg of Zinc.

9. A formulation consisting of:
MCT oil from about 1 gram to about 40 grams;
Ketone salts/esters from about 5 grams to about 40 grams;
Coconut oil extracts from about 1 gram to about 80 grams;
Cannabidiol from about 1 mg to about 800 mg;
Tetrahydrocannabinol from about 1 mg to about 800 mg;
Mixed cannabinoids from about 5 mg to about 1200 mg;
Bergamot from about 500 mg to about 1500 mg;
Chokeberry berry from about 50 mg to about 1,000 mg;
Curcumin from about 100 mg to about 1500 mg;
Flavonoids from about 100 mg to about 1200 mg;
Grape seed about 50 mg to about 500 mg;
Olive leaf from about 25 mg to about 400 mg;
Spearmint from about 500 mg to about 2000 mg;
Tea from about 25 mg to about 1000 mg;
Damiana from about 100 mg to about 600 mg;
Maca from about 50 mg to about 500 mg;
*Tribulus* from about 10 mg to about 400 mg;
Vitamin B3 from about 1 mg to about 35 mg;
Nicotinamide riboside from about 100 mg to about 2000 mg;
Vitamin B6 from about 1 mg to about 20 mg;
Vitamin B9 from about 100 mcg to about 1000 mcg;
Vitamin B12 from about 1 mcg to about 200 mcg;
Natural carotenes from about 1 mg to about 60 mg);
Lutein from about 6 mg to about 20 mg;
Zeaxanthin from about 0.1 mg to about 5 mg;
Choline from about 25 mg to about 600 mg;
L-carnitine from about 25 mg to about 750 mg;
Vitamin C from about 50 mg to about 2000 mg;
Vitamin E from about 5 IU to about 400 IU;
Alpha lipoic acid from about 10 mg to about 150 mg;
Co-enzyme Q-10 from about 5 mg to about 120 mg;
N-acetyl cysteine from about 50 mg to about 500 mg;
Chromium from about 10 mcg to about 120 mcg;
Magnesium from about 25 mg to about 500 mg;
Selenium from about 10 mcg to about 150 mcg;
Zinc from about 1 mg to about 80 mg;
and mixtures and combinations thereof; and
wherein said formulation is admixed prior to being administered to an individual in a single medium.

10. A method of manufacturing a formulation, said method comprising admixing at least one ketogenic agent, at least one cannabinoid, at least one polyphenol, at least one phytonutrient, at least one dietary nutrient, at least one antioxidant, and at least one mineral, or any mixtures or combination thereof in varying amounts, wherein said formulation is admixed into a single medium prior to being administered to a user, said at least one ketogenic agents is selected from a group consisting of MCT oil, ketone salts/esters, and coconut oil extracts, and mixtures and combinations thereof, and said at least one cannabinoid is selected from a group consisting of cannabidiol, tetrahydrocannabinol, mixed cannibinoids, and mixtures and combinations thereof, said at least one polyphenol is selected from a group consisting of bergamot, chokeberry, curcumin, flavonoids, grape seed, olive leaf, spearmint, tea, and mixtures and combinations thereof, said at least one phytonutrient is selected from a group consisting of Damiana, Maca, *Tribulus*, and mixtures and combinations thereof, said at least one dietary nutrient is selected from a group consisting of Vitamin B3, Nicotinamide riboside, Vitamin B6, Vitamin B9, Vitamin B12, natural carotenes, lutein, Zeaxanthin, Choline, and L-carnitine, and mixtures and combinations thereof, said at least one antioxidant is selected from a group consisting of Vitamin C, Vitamin E, Alpha lipoic acid, Co-enzyme Q-10, N-acetyl cysteine, and mixtures and combinations thereof, and said at least one mineral is selected from a group consisting of Chromium, Magnesium, Selenium, and Zinc, and mixtures and combinations thereof.

* * * * *